United States Patent [19]

Sullivan et al.

[11] Patent Number: 4,849,352
[45] Date of Patent: Jul. 18, 1989

[54] ANTIBODY PURIFICATION PROCESS

[76] Inventors: John B. Sullivan, 6181 E. Country Club Vista Dr., Tucson, Ariz. 85715; Findlay E. Russell, 3437 E. Bunell St., Tucson, Ariz. 85716

[21] Appl. No.: 659,629

[22] Filed: Oct. 9, 1984

[51] Int. Cl.$^4$ .............................................. C12P 21/06
[52] U.S. Cl. ....................................... 435/69; 435/68; 435/180; 436/512
[58] Field of Search ........................... 435/68, 69, 180; 436/512

[56] References Cited

U.S. PATENT DOCUMENTS 4,012,502  3/1977  Philpot .................................. 424/98

OTHER PUBLICATIONS

Bernfeld—Science, 142:678–679, (1963).
Martinez-Hernandez et al.—Journal of Histochemistry and Cytochemistry, 23(2):146–148, (1975).
Sullivan et al.—Proc. West. Pharmacol. Soc., 25:185–192, (1982).
Otten—American Journal of Emergency Medicine, 1:83–93, (1983).
Smith et al.—Clin. Exp. Immunol., 36:384–396, (1978).
Carrel et al.—Nature, 221:385–386, (1969).
Nisonoff—A. Methods Medical Res., 101:134–141, (1964).
Kolb et al.—Chem. Abst., vol. 97, (1982), p. 90190s.
Coulter et al.—Chem. Abst., vol. 99, (1983), p. 3883v.

Primary Examiner—Sam Rosen
Attorney, Agent, or Firm—Dorr, Carson, Sloan & Peterson

[57] ABSTRACT

F(ab) fragments are isolated from an antibody containing source by contacting the antibody containing source with a papain-polyacrylamide matrix to produce F(ab) and F(c) fragments which are then passed through an antigen-polyacrylamide gel capable of attracting the F(ab) fragments. F(ab)$_2$ fragments are obtained by contacting the antibody containing source with a pepsin-polyacrylamide matrix to produce F(ab)$_2$ and F(c) fragments which are then passed through an antigen-polyacrylamide gel capable of attracting the F(ab)$_2$ fragments. IgG antibodies are obtained by passing an antibody containing source through an antigen-polyacrylamide gel. These processes can be used to purify a wide variety of antibodies which can be used as therapeutic agents and as diagnostic agents. Antivenins produced by these processes have substantially reduced foreign protein levels and hence are less likely to produce immunogenic reactions. Bulk, unprocessed antibody sources may be utilized and, for reasons of process simplification, are preferred.

16 Claims, 8 Drawing Sheets

FIG. 1

IMMUNOELECTROPHORESIS
(I)

| | | |
|---|---|---|
| IgG (stnd) | | (ANTI-) |
| WPCA | | IgG H+L |
| IgG (stnd) | | T chain |
| IgG (AP) | | T chain |
| 4 hr. digest (Fab) | | IgG H+L |

IMMUNOELECTROPHORESIS (II)

IMMUNOELECTROPHORESIS
(III)

FIG. 4

IMMUNOELECTROPHORESIS
(IV)

4 hr. digest Fab 4 hr. digest Fab       ∝ IgG  H+L 4 hr. digest Fab       ∝ IgG (T)

4 hr. digest Fab       ∝ F(ab)$_2$ 4 hr. digest Fab       ∝ F(c)

4 hr. digest Fab

SCHEME OF PRODUCTION AND PURIFICATION SYSTEM

— NOTE TWO ARCS

FIG. 8

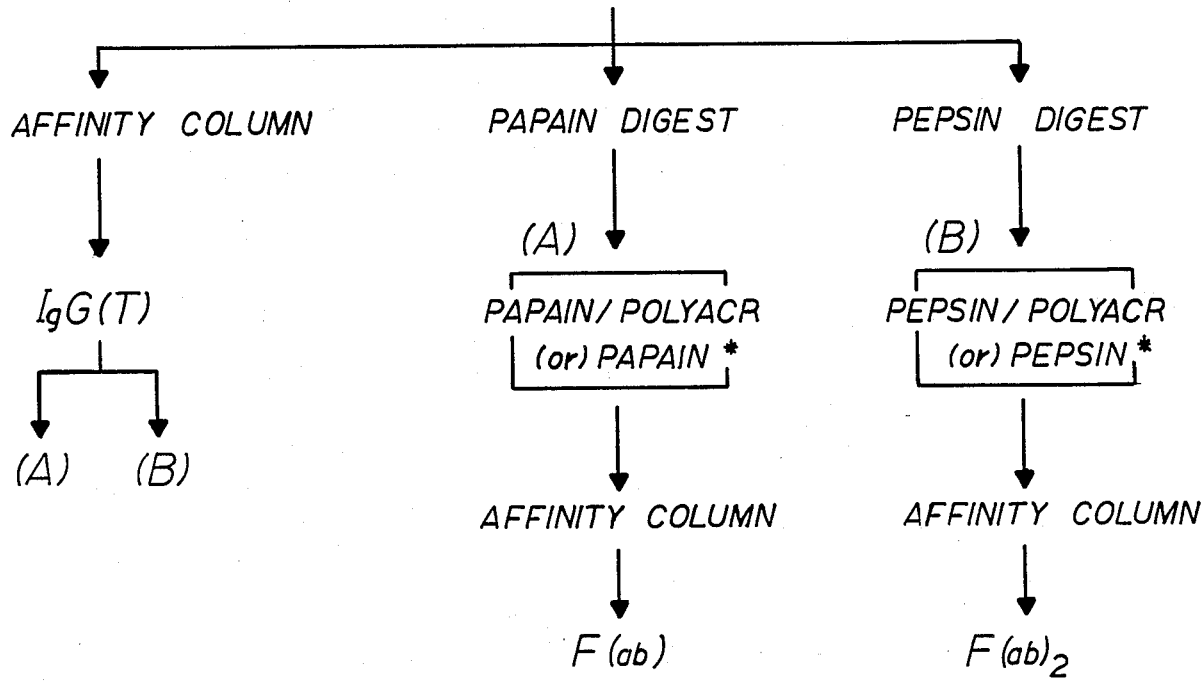

\* By modification of traditional method or by traditional method

SCHEME OF ISOLATION OF IgG(T), POLYVALENT AND MONO-VALENT, AS WELL AS PRODUCTION AND ISOLATION OF ANTI-BODY FRAGMENTS, POLYVALENT AND MONOVALENT. PROCESS CAN BE USED TO ISOLATE MONOCLONAL ANTIBODIES AND MONOCLONAL FRAGMENTS AS WELL AS ANTIBODIES AND FRAGMENTS OF ANTIBODIES TO ANTIGENS IMMOBILIZED IN THE POLYACRYLAMIDE. THE ANTIBODY CAN BE ISOLATED INITIALLY AND THEN DIGESTED BY EITHER A OR B, FOLLOWED BY FRAGMENT ISOLATION.

ANTIBODY PURIFICATION PROCESS

FIELD OF THE INVENTION

This invention generally relates to processes for purifying antibodies. More specifically it relates to antibody purification by affinity chromatography processes using polyacrylamide gels.

BACKGROUND OF THE INVENTION

It is well known that antigen-polyacrylamide gels can be used to entrap antibodies. It is also well known that certain enzymes, e.g., trypsin, amylase and ribonuclease have been entrapped and used as attractive antigens in such gels (Science 142:678–679, 1963). Antigens can also be purified in a similar manner using specific antibodies in the acrylamide gels to attract the antigens (Journal of Histochemistry and Cytochemistry, 23(2):146–148, 1975). These tendencies for certain antibodies and antigens to attract one another can be put to practical use. For example, an affinity chromatography procedure using a venom-polyacrylamide gel has been used to further purify equine source antivenin (Proc. West. Pharmacol. Soc. 25:185–192, 1982). That is to say, venom-polyacrylamide gels have been used to further purify a commercially available antivenin, Antivenin (Crotalidae) Polyvalent ("ACP"-Wyeth Laboratories, Box 8299, Philadelphia, Pa., U.S.A.) which is normally purified by ammonium sulfate precipitation procedures (American Journal of Emergency Medicine, 1:83–93, 1983). It is also well known that various enzymes such as trypsin, chymotrypsin and papain can be used to split antibody molecules into fragments having higher activities and lower toxicities than the original antibody molecule (see for example, U.S. Pat. No. 4,012,502). Such procedures normally involve removing desired antibody containing protein fragments in a fractionating column, solution digesting these antibody containing protein fragments with various enzymes and then isolating the sought after antibody fragments in Sepharose columns.

Conceptually, a whole antibody molecule, commonly referred to as IgG, is often thought of as being comprised of three fragments connected in a Y shape. The two upper fragments are each referred to as F(ab) fragments. The stem of the Y is commonly referred to as the F(c) fragment. Each of the F(ab) fragments can be split from each other and from the F(c) fragment. The whole antibody, IgG molecule can also be cleaved into a larger fragment commonly referred to as a $F(ab)_2$ fragment and a F(c) fragment. This cleavage takes place in such a manner that an $F(ab)_2$ fragment is comprised of two attached F(ab) fragments. It is well known in the art that exposure of IgG molecules to papain produces F(ab) fragments and that pepsin digestion produces $F(ab)_2$ fragments. It is also well known in the art that the smaller F(ab) fragments are less likely to cause undesired immunogenic reactions. A general rule is that, given possession of the antibody active site, the smaller the antibody molecule the better.

IgG, F(ab) fragments and $F(ab)_2$ fragments often have separate utilities. Furthermore, F(ab) and $F(ab)_2$ fragments may sometimes be utilized together. Hence processes for obtaining antibodies in each of these forms are highly desirable. For example, F(ab) fragments have the same affinity for antigens as IgG molecules, but they have lower molecular weights. Consequently, for reasons hereinafter more fully discussed, they can be more quickly distributed in the body and then filtered and excreted by the kidney. IgG molecules on the other hand are generally too large to be excreted by kidney functions. This means that whole IgG cannot distribute to tissue sites and neutralize toxins similar to F(ab) nor can the IgG and toxin combination be excreted by kidneys. However, IgG molecules can perform other useful functions. The F(c) portion of their molecule normally acts as a signal marker for lymphocytes to recognize and phayocytize. This is the chief pharmacological reason for leaving an IgG molecule intact. If for example a sought after antigen molecule is already a large molecule, the use of F(ab) fragments is limited. Even though the F(ab) fragments can be used to neutralize large antigen molecules, the kidneys still will not be able to excrete them. In such cases it may be better to use a whole IgG molecule to find the large antigen molecule so that the entire molecule assembly is phagocytized. See for example, Clin, Exp. IMMUNOL, 36:384–396(1979).

Another advantage to having the ability to break IgG antibodies into F(ab) or $F(ab)_2$ fragments is found in the pharmacological concept of volume of distribution. Volume of distribution is that volume of the body in which a given drug is dissolved. Circulating blood has a certain volume, but the body's water volume is much greater. For most IgG proteins, the volume of distribution is limited to the volume of circulating blood. However, for smaller molecules such as F(ab) fragments, the volume of distribution may be the total volume of body water. Furthermore, smaller molecules such as F(ab) fragments often have the ability to cross certain physiological systems and barriers such as, for example, the blood/brain barrier. Larger antibodies do not have this capability. Consequently, neurotoxins may not be accessible to IgG molecules since the IgG molecules are confined to the circulating blood system. However many neurotoxins, including some snake venoms, may be accessible to F(ab) fragments because F(ab) fragments usually have a volume of distribution which includes water; hence the F(ab) fragments may be capable of crossing the blood/brain barrier in both the incoming and outgoing directions. In such cases F(ab) fragments may be used to excrete many kinds of neurotoxins which are not otherwise accessible to IgG antibodies. Thus from both the pharmacological and toxicological point of view, the ability to separate and purify a given antibody into selected fragments is of great significance to its application.

Antibody purity is a particularly important issue in the antivenin preparation art. Antivenin is a suspension of venom-neutralizing antibodies prepared from the serum of animals (typically horses) hyperimmunized against a specific venom or venoms. Horse and other animal serums are often digested with pepsin to obtain antivenin agents which are then precipitated out of the solution. Monovalent Bothrops (Laboratories "MYN", S.A., Av. Coyoacan 1707, Mexico City 12, D.F., Mexico), Anticrotalic (Instituto Butantan, Ciaxa Postal 65, Sao Paulo, Brazil) and Centiviperin (Institute Pasteur d'Algerie, Rue Docteur Laveran, Alger, Algeria) are examples of antivenin antibodies which are pepsin digested and then precipitated with ammonium sulphate.

Unfortunately, such enzyme digestion and ammonium precipitation procedures do not remove all foreign proteins from horse serum derived antivenins. Consequently, some bite victims undergoing antivenin treatment suffer extreme life threatening allergic reactions to those foreign proteins which are not removed from the horse serum by prior art purification procedures. Less life threatening serum sickness reactions are also common. The exact mechanism for these allergic reactions has not been elucidated. For example they do not appear to be precisely related to previous exposure to horse antigen. Many researchers believe they may be due to anticomplementary activity of the serum. Another school of thought takes the position that the purity of the antivenin rather than the origin of the serum is the more critical factor in such allergic reactions. As a precaution however, all patients with known allergies to horses or horse serum are normally regarded as being at risk for serious anaphylactic reactions if given horse serum antivenin without adequate preparation. Therefore, any new and more efficacious procedures for purifying antibodies in general should be considered as being particularly important to the antivenin preparation art.

SUMMARY OF THE INVENTION

This invention discloses the use of enzymoabsorbed affinity methods combined with reversible immunoabsorption chromatography procedures to produce and isolate F(ab) and F(ab)$_2$ fragments to any antigen. The overall procedure is, however, especially useful in producing and isolating F(ab) and F(ab)$_2$ fragments to snake venoms as well as other venoms. Another disclosed immunoabsorption procedure can be utilized to produce a highly refined IgG antibody from a bulk antibody source. Furthermore, the processes of this invention are capable of producing antibodies without recourse to certain precipitation procedures employed in the prior art. The F(ab) fragments, F(ab)$_2$ fragments and IgG thus produced are more highly purified, have greater antibody activities and are less likely to produce immunogenic reactions than their counterpart antibodies produced by processes utilizing such precipitation procedures. Furthermore, these antibody fragments can be products from monovalent, polyvalent and monoclonal sources. For example, F(ab) fragments can be produced by digesting either polyvalent IgG(T) or polyvalent anti-horse serum by methods wherein the papain is not bound to the polyacrylamide a well as by methods wherein the papain is bound to polyacrylamide as an enzymatic affinant. In a preferred embodiment of this invention each of the above antibodies is produced from bulk antibody sources.

The overall test procedures used to establish this invention began with an enzyme digestion of the antibody source. First, a papain-polyacrylamide matrix or a pepsin-polyacrylamide matrix was established to receive the antibody containing source. Again, the antibody containing source may vary considerably. For example, in the context of antivenin purification, the antibody source may be bulk, unprocessed hyperimmune equine serum, laboratory produced monoclonal antibodies or commercially available antivenins. Those skilled in the art will appreciate that F(ab) fragments (papain digest) or F(ab)$_2$ fragments (pepsin digestion) and their respective F(c) fragments can be produced from many other kinds of antibody sources. For example, the processes of this invention were also specifically employed to isolate hemagglutinin specific antibody to an influenza virus. The literature also suggests that purification of many other antibodies by use of the processes of this invention can be accomplished since specific antibodies to kidney basement membrane antigens, to human chorionic gonadotropin, to bovine serum albumin and to human immunoglobulin A each have been produced by analogus purification techniques. Antigens also can be isolated by these procedures since entrapped antibodies can be used to attract the antigens (see generally, J. Histochem. Cytochem. 23(2):146–148, 1975). However, this method is less preferred since, when this is done, much more antibody must be entrapped to ensure that available antigenic sites are on the surface of the gel fragments. Moreover, human IgG also can be entrapped and used to isolate anti-IgG antibodies (see generally, Nature, 221:385–386, 1969).

Other variations of this invention are also possible. For example, antibodies to venom proteins have been immobilized on other matrices, such as cyanogen bromide activated sepharose, and used to isolate specific venom proteins (Period. Biol. 80, Supp. 1: 97–100 (1978). However, heretofore, enzymes such as papain and pepsin have not been used to digest whole IgG to their relevant F(ab) and F(ab)$_2$ fragments which are then collected by affinity chromatography procedures. Furthermore, for reasons hereinafter discussed, the fact that such antibodies can be directly obtained from bulk or monoclonal sources is particularly noteworthy. Regardless of the source of the antibody, however, the purification process of this invention continues by capturing antibodies on an antigen-polyacrylamide affinity chromatography gel which has embedded within its matrix, an antigen with an affinity for the sought after antibody. In the alternative, an affinant having an affinity for the F(c) fragments may also be employed.

To prove the efficacy of our process, the captured antibodies were then separated from the polyacrylamide and compared to counterpart fragments or IgG produced from comparable antibody containing sources, which were produced by other purification procedures. For example F(ab) fragments produced directly from bulk, unprocessed hyperimmune equine serum by the process of this invention were compared by immunoelectrophoresis diagrams to F(ab) fragments produced from commercially available equine serum. As previously noted, these serums are purified by known ammonia sulfate precipitation procedures. The commercial serums were then subjected to papain digestion and affinity chromatography procedures to produce F(ab) fragments which are compared to the F(ab) fragments produced directly from the bulk source without the ammonium sulfate precipitation step normally employed in the production of the commercial antivenin. Thereafter, the F(ab) fragments produced by the process of this invention were also compared to the commercial antivenin with respect to their relative lethality-neutralizing abilities. These tests clearly established that the F(ab) fragment antibodies and IgG produced by the processes of this invention afford better protection against venom-induced pathophysiology than the commercial antivenin on a milligram per milligram basis.

Those skilled in the art will appreciate that when pepsin, rather than papain, is embedded into the acrylamide matrix, F(ab)$_2$ rather than F(ab) fragments are obtained. Again bulk, monoclonal and partially purified commercial antibody sources may be used. Monovalent and polyvalent fragments can be produced. Such F(ab)$_2$ fragments should also afford greater protection against venom-induced pathophysiology than the commercial antivenin. Similarly, they should produce less acute hypersensitivity reactions than those produced by the commercial antivenin.

Furthermore, according to the antigen-polyacrylamide affinity chromatography aspects of this invention, IgG antibody molecules also can be directly purified from bulk sources or monoclonal sources. They can be produced by passing a bulk antibody source or a monoclonal antibody source through an affinity chromatography system having an antigen-polyacrylamide matrix. This matrix attracts the IgG antibodies which can then be isolated from the gel matrix by procedures such as those found in the examples disclosed in later portions of this patent disclosure. Such IgG molecules are also largely characterized by the fact that they too are more efficacious than commercial antivenin and they too tend to produce fewer and/or less severe allergic reactions than those IgG molecules which have not been processed in the antigen-acrylamide affinity column system of our invention. The inventive aspect of this patent disclosure with respect to IgG molecules produced in this way is the fact that IgG can be pulled directly from bulk sources and not just refined from partially purified sources as taught in the previously noted Proc. West. Pharmacol. Soc. article.

In a variation of the process taught by this invention, F(ab) fragments are produced by passing an antibody source (bulk, monoclonal or partially purified) through a first and a second affinity chromatography system. The first affinity chromatography system has a papain-polyacrylamide gel matrix. This system also splits IgG molecules within the antibody source into F(ab) fragments and F(c) fragments. The effluent from the first affinity chromatograph system is then fed into the second affinity chromatography system which has an antigen-polyacrylamide gel matrix. This matrix attracts the F(ab) fragments which can then be isolated from the gel matrix by known procedures hereinafter described. Here again, the antigen embedded in the polyacrylamide gel matrix can be varied greatly to obtain other useful results. For example, when whole influenza virus was used as the embedded affinant; our process isolated a hemagglutinin specific antibody and enriched it from 1,000 to 2,000 fold over a common antisera preparative process. The HAI titer was enriched by a factor of two and the protein content decreased 500 fold.

As previously noted, an antibody rather than the antigen can be embedded in an acrylamide matrix to pick up a relevant antigen. This fact can be utilized in designing an immunodetection system which can also be used in the context of envenomation. For example plasma can be passed over such a column to determine if antibodies are being produced by the victim. The kind and degree of such antibody product can form the basis of such an immunodetection. Likewise the F(c) fragment, rather than the F(ab) fragment may be captured by an appropriate antigen affinant.

Furthermore, F(ab)$_2$ fragments may be produced by passing an antibody source (bulk, monoclonal or partially purified) through a first and a second affinity chromatography system. The first affinity chromatography system will have a pepsin-polyacrylamide gel matrix. This matrix splits the IgG molecules within the antibody source into F(ab)$_2$ fragments and F(c) fragments. The effluent from the first system is then fed into the second affinity chromatography system which has an antigen-polyacrylamide matrix. This matrix attracts the F(ab)$_2$ fragments which are then isolated from the gel matrix.

In a representative example of this process, F(ab) antivenin fragments are produced by contacting bulk, unprocessed hyperimmune equine serum (i.e., untreated by any solution enzyme digestion or ammonium sulphate precipitation processes) with a papain-polyacrylamide matrix prepared as follows. An acrylamide monomer (16% acrylamide, 4% N, N-methylene-bisacrylamide)/papain mixture is polymerized by the addition of 0.4% ammonium persulfate in water and TEMED (N,N,N-N-tetramethylenediamine). The mixture is well mixed and a water layer used to exclude oxygen. After polymerization, the papain-polyacrylamide matrix thus formed is fractionated by forcing the gel through a small porosity stainless phosphate buffered saline (pH 7.4) until all fines are removed. The gel is then packed into a column and washed alternately with PBS and 0.1M glycine-HCL (pH 2.5). During this washing the effluents are monitored with a spectrophotometer (280 nM). The washing cycle is continued until a baseline reading is obtained on the spectrophotometer. The matrix-papain fractionated gel is then placed into a beaker with a papain solvent (0.5M phosphate pH 8, 0.002 M EDTA, and 0.01M cysteine) containing cysteine that activates the enzyme. Bulk, unprocessed hyperimmune serum is then stirred in with the papain-polyacrylamide fractionated gel. This stirring is at room temperature but can be done at 37° C. to speed the digestion. Initial experiments have demonstrated that digestion of antisera begins soon after the serum is introduced and can be nearly completed in about four hours at room temperature. The papain digestion produces F(ab) fragments from the antivenin. The resulting mixture containing these F(ab) fragments is then introduced into an affinity chromatography column employing rattlesnake venom as the (affinant) antigen. The venom is embedded in the polyacrylamide by a polymerization process which is substantially the same as the process just described with respect to the formation of the papain-acrylamide gel. An initial peak eluted with PBS consists of foreign protein. After the effluent is returned to baseline, the solvent is changed to glycine-HCl. A second peak is eluted which consists of purified F(ab) antivenin fragments which are collected separately and thereafter used as therapeutic agents.

The specificity of the F(ab) fragments produced from the bulk, unprocessed hyperimmune equine serum is then compared, by immunoelectrophoresis methods hereinafter described, to the F(ab) fragments produced from a commercial antivenin which was further purified by the affinity chromatography process taught in the previously cited Proc. West. Pharmacol. Soc. publication. The F(ab) fragments from these two different sources are the same. Hence applicants have negated the need for the ammonium sulfate precipitation procedures used in producing commercial antivenins. The F(ab) and F(ab)$_2$ fragments produced by this invention are believed to be proteins or polypeptides. The F(ab) antivenin fragments thus produced have a molecular weight of about 50,000 and the F(ab)$_2$ fragments have a molecular weight of about 100,000. The IgG molecules derived from bulk sources have a molecular weight of about 150,000. Lethality and inhibition experiments were then conducted to compare the antivenin activity of the F(ab) fragments to the antivenin activity of commercial antivenin. These experiments indicate that the F(ab) fragments have a far greater antivenin activity than antivenins produced by the ammonium sulfate precipitation procedures used in the production of commercial antivenins. Furthermore, this increased activity can be achieved with fewer and less severe allergic reactions since the active site remains on the F(ab) fragment while portions of the original protein molecules which are antigenic to humans are removed by the processes of this invention. A reduced level of immogenic reaction with respect to the IgG is demonstrated in applicants' previously cited Proc. West. Pharmacol. Soc. publication.

DESCRIPTION OF THE DRAWING

FIG. 1 depicts immunoelectrophoresis diagrams of various forms of IgG.

FIG. 4 depicts immunoelectrophoresis of 4 hour digests of F(ab) antibody materials.

FIG. 8 is a schematic representation of the application of the process of this invention of a polyvalent or monovalent antisera.

DETAILED DESCRIPTION OF INVENTION

Papain-Polyacrylamide Matrix Preparation

A representative affinity papain-polyacrylamide matrix is prepared by adding 1500 ml of soluble papain (Sigma Chemical Company, P.O. Box 14508, St. Louis, Mo., 63178), to 20 mls. of acrylamide and bisacrylamide monomer (27 mg/ml protein; 24 units/ug protein; 30.5 mg total protein; 732 units total in 20 mls.) Those skilled in the art will appreciate that other matrix forming materials could be used in the practice of this invention; however, acrylamide is highly preferred since it costs less than most other similar materials, it polymerizes quickly, its protein retention and efficiency are high, it can be fractionated easily to provide a uniform matrix and it is reusable and stores easily. In any event, after the papain is dissolved in the monomer solution, polymerizing agents, N,N,N-N-tetramethylethylene-diamine (TEMED) and 0.4% ammonium persulfate are added. After being formed, the resulting matrix is fractionated by forcing it through a stainless steel screen having a pore dimension of 0.3 mm. The fractionated matrix is washed 5 times with phosphate buffered saline (PBS) to rid the matrix of nonusable fine particulate matter. The matrix is then washed with alternating solutions of PBS and 0.1 M glycine (pH2.5) and monitored with a 280 nM ultraviolet detector. This assures that any extraneous papain or other foreign materials are removed. Preferably, the papain/polyacrylamide matrix is immersed in a buffer solvent comprised of 0.5M phosphate (pH 8.0); 0.002 M EDTA; and 0.01M cysteine. The immersed matrix is then ready to receive an antibody source. Twenty mls. of bulk hyperimmune equine serum is added to a beaker containing the papain-acrylamide buffer mixture and stirred for four hours (digestion periods from about 1 hour to about 48 hours are preferred and periods of from about 4 to 8 hours are most preferred). The resulting F(ab) containing solvent digest is then separated from the papain-acrylamide matrix by affinity chromatography. The digest is then passed over through representative antigen-polyacrylamide affinity chromatography columns prepared as follows.

Antigen-Polyacrylamide Column Preparation

Figure 5:
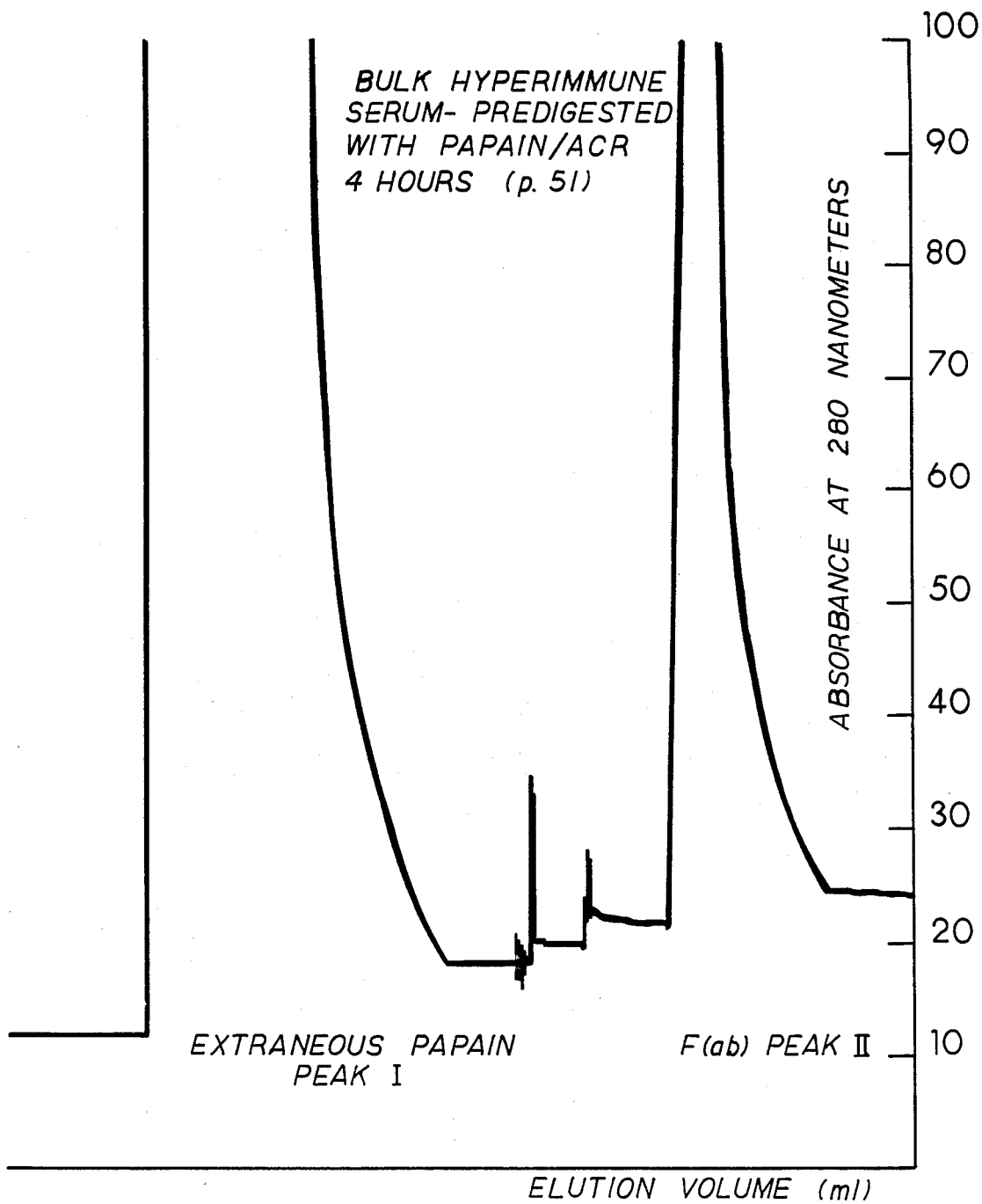
FIG. 5 is an elution diagram of the materials eluted from an antigen-polyacrylamide affinity column.

Representative antigen-polyacrylamide gels used in establishing the antivenin aspects of this invention were prepared from venom taken from four rattlesnake species *Crotalus atrox, C. adamanteus, C. scutulatus scutulatus* and *C. viridis helleri*. Each sample was prepared in a separate column so that each venom could be tested as an affinant. One hundred mg of each venom were dissolved in separate 10 ml portions of acrylamide monomer (16% acrylamide, 4% N, N-methylenebisacrylamide) in PBS, pH 7.4, in a small beaker. Polymerization of the venom-acrylamide mixtures were achieved by addition of 500 ul of 0.4% ammonium persulfate in water and 50 ul of TEMED. The mixture is mixed well and water was layered over the surface to exclude oxygen. The venom-acrylamide mixture gelled in 10 minutes and was fractionated by forcing the broken pieces through a stainless steel mesh (0.3 mm). After fractionation the venom-polyacrylamide gel was reduced to a particle consistency. This fractionated gel was defined 5-6 times with PBS and packed by gravity into columns 1 cm×20 cm. The venom-polyacrylamide columns were washed with alternating cycles of PBS and 0.1 M glycine, pH 2.5 (0.1 M glycine, 0.154 M Na Cl, pH adjusted with HCl) until a steady baseline was obtained by monitoring the effluent at 280 nM with a spectrophotometer. The column was returned to pH 7.4 with PBS and was then ready to receive the solution containing F(ab) fragments produced by the papain-polyacrylamide digestion previously described. The solution containing the F(ab) fragments is passed through the column to attract the F(ab) fragments to the antigen (venom). The solution, diluted to 10 mls, was added with a PBS mobile phase. The effluent flow was monitored at 280 nM ultra violet detection. The results of this elution are depicted in FIG. 5. An initial peak I eluted with PBS is extraneous protein. Peak II is eluted with 0.1M Glycine, pH 2.5, after baseline stabilization. This peak II contains the F(ab) material. This material can be collected and the pH of the system restored to 7 with Tris buffer. The collected material is then dialyzed against distilled water (approximately 24 hours) and lyophilized for storage at −20° C.

Affinity Isolation of IgG

Columns prepared by the procedures taught in the above discussion, i.e., "Antigen-Polyacrylamide Column Preparation", can also be used to isolate IgG from bulk sources. PBS was used as the initial solvent. A first peak similar to that in FIG. 5 contains extraneous protein. After the baseline was re-established, 0.1M glycine-HCl, pH 2.5 solvent was used to elute off a second peak which contains the IgG. The pH of the IgG antibody effluent is adjusted to 7.4 with TRIS buffer. The isolated, purified antibody effluent is dialyzed against distilled water for 24 hours at 10° C., lyophilized and stored at −20° C. This IgG antivenin can be isolated to each of the four venoms tested.

Figure 6:
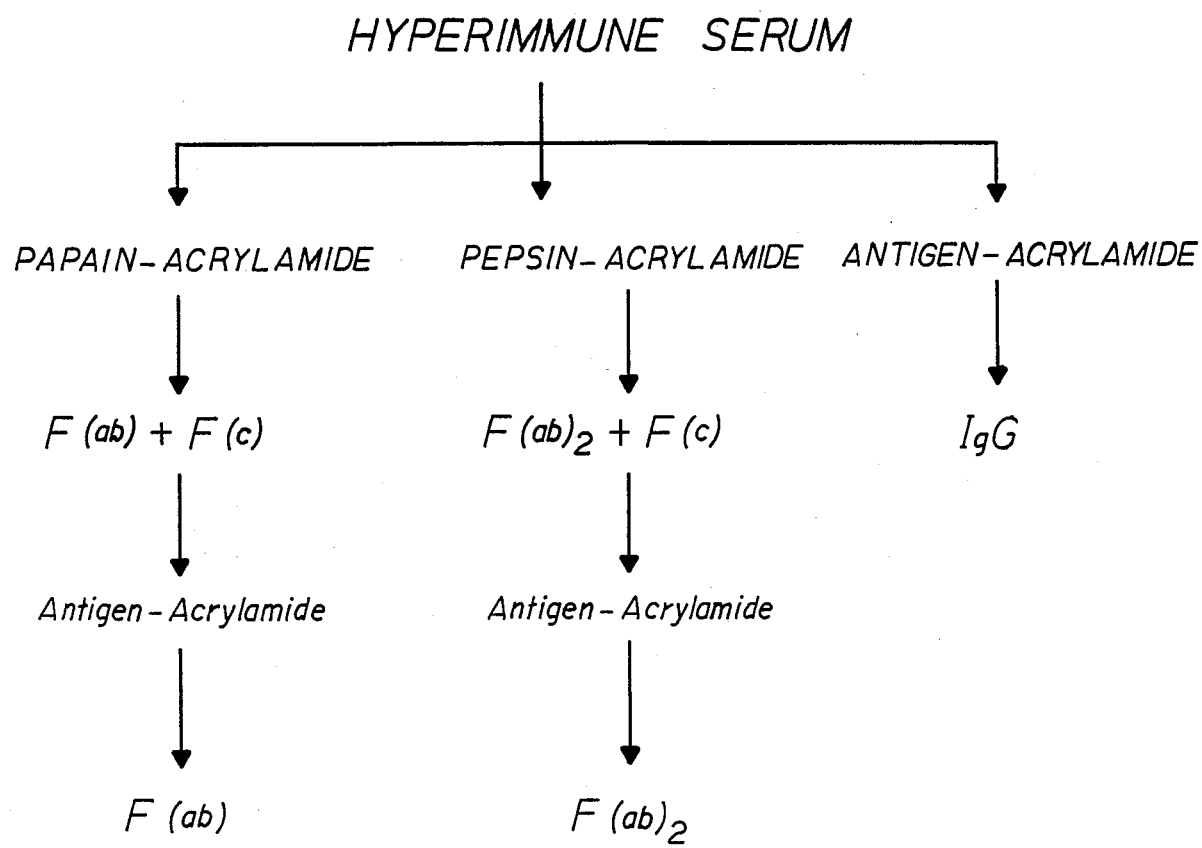
FIG. 6 is a schematic presentation of the relationship of the processes of this invention.

Again it should be noted that the previously cited Proc. West. Pharmacol. Soc. article teaches that such antigen-polyacrylamide affinity columns can be used to further purify commercial antivenin produced by ammonium sulfate precipitation procedures. However, in view of the problems of competitive reactions of proteins, and protein affinity for like proteins, it is surprising that this antigen-polyacrylamide column also has the ability to pull otherwise untreated IgG directly out of a bulk source such as a hyperimmune serum. A schematic relationship showing each of the steps of the processes of this invention, as applied to antivenin purification from a bulk source, is depicted in FIG. 6.

Derivation of F(ab) Fragments from ACP

In order to determine that F(ab) fragments produced by the processes of this invention are similar to the F(ab) fragments which can be derived from commercial antivenin, the following test procedure was utilized. First, Wyeth Antivenin (Crotalidae) Polyvalent (ACP) was purified by the affinity chromatography processes taught in the previously noted Proc. West. Pharmacol. Soc. article. The resulting IgG antibodies are then digested by the papain-polyacrylamide digestion procedures taught in the "Papain-Polyacrylamide Matrix Preparation" section of this patent application. The resulting F(ab) fragment containing solution is then introduced into a venom-polyacrylamide affinity column prepared according to the procedures taught in the "Antigen-Acrylamide Column Preparation" section of this patent application. Again, a first PBS eluted peak contains extraneous protein materials. After re-establishing a baseline, 0.1M glycine HCl pH 2.5, is again used to elute off a second peak which contains F(ab) fragments. These first and second peaks are substantially identical to those obtained (see FIG. 5) when F(ab) fragments are derived from bulk, unprocessed hyperimmune serum by the conjunctive use of the procedures described in the "Papain-Polyacrylamide Matrix Preparation" and "Antigen-Polyacrylamide Column Preparation" sections of this patent disclosure.

The F(ab) fragments from ACP are also compared with the F(ab) fragments from bulk sources on the basis of their immunoelectrophoresis diagrams. For example the immunoelectrophoresis diagrams of FIG. 1, when taken in conjunction, show that the affinity purified ("AP") IgG is mainly IgG(T), the 4 hour F(ab) digest does not precipitate against IgG heavy and light chains, and that the IgG (AP) does not precipitate against heavy and light chains. The anti-IgG(T) sample is placed in this test to see how much anti-T the standard IgG has compared to an affinity purified IgG (designated "IgG(AP)"). Applicants' IgG (AP) is very heavy in IgG (T). Other immunoelectrophoresis tests have shown that when applicants' IgG(AP) is immodiffused against IgG(T), the results indicate that the IgG(AP) is solely IgG(T) and not IgG. Neither the IgG(AP) nor the 4 hour digest react against normal IgG of the horse serum heavy or light chain. The fact that our IgG(AP) reacts against the T chain, but not against the H and L, indicates that it is predominantly IgG(T). Therefore we are isolating the high affinity antibody.

Figure 2:
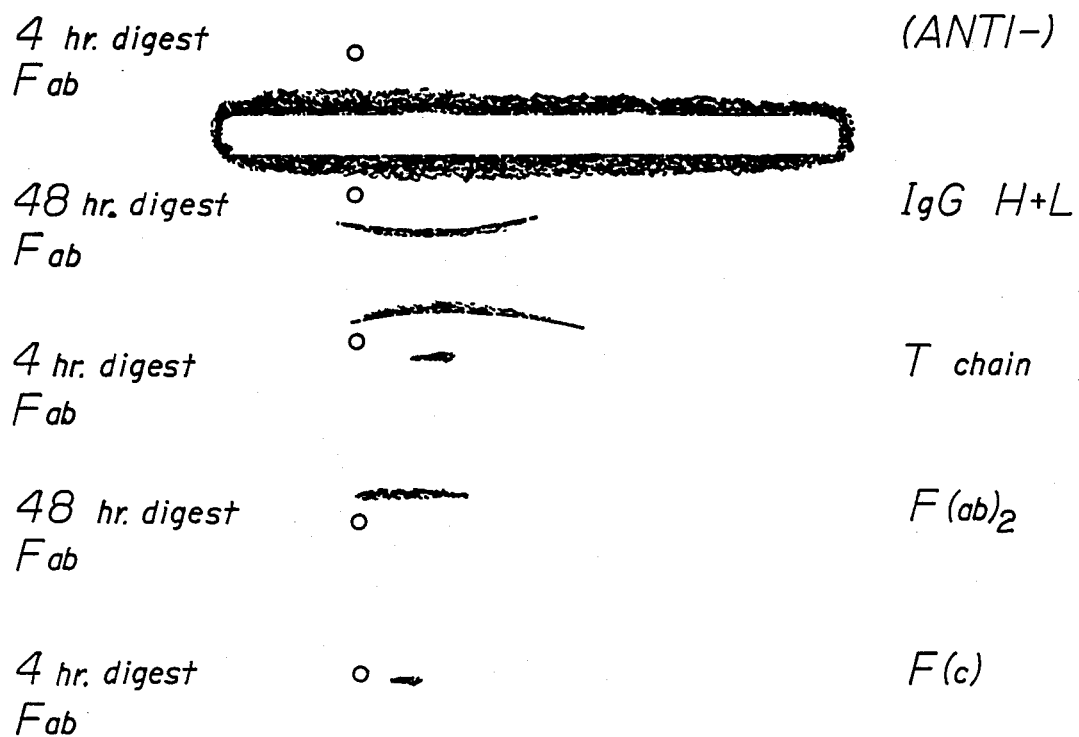
FIG. 2 depicts immunoelectrophoresis of 4 hour and 48 hour digests of F(ab) antibody materials.

Taken in conjunction, the immunoelectrophoresis diagrams of FIG. 2 show that the 48 hour digest product and the 4 hour digest product each precipitate bands against anti-F(ab)2 but not against anti-F(c). No reactions against IgG heavy and light chains are evident. The reactions against the anti-IgG(T) are strongly evident. An anti-F(ab)2 fragment shows a strong 48 reaction. A weaker 4 hour digestion reaction is shown. Taken in total, this evidence indicates that both the F(ab) fragments from the 48 digestion and the F(ab) fragments from the 4 hour digestion derive from the IgG(T).

Figure 3:
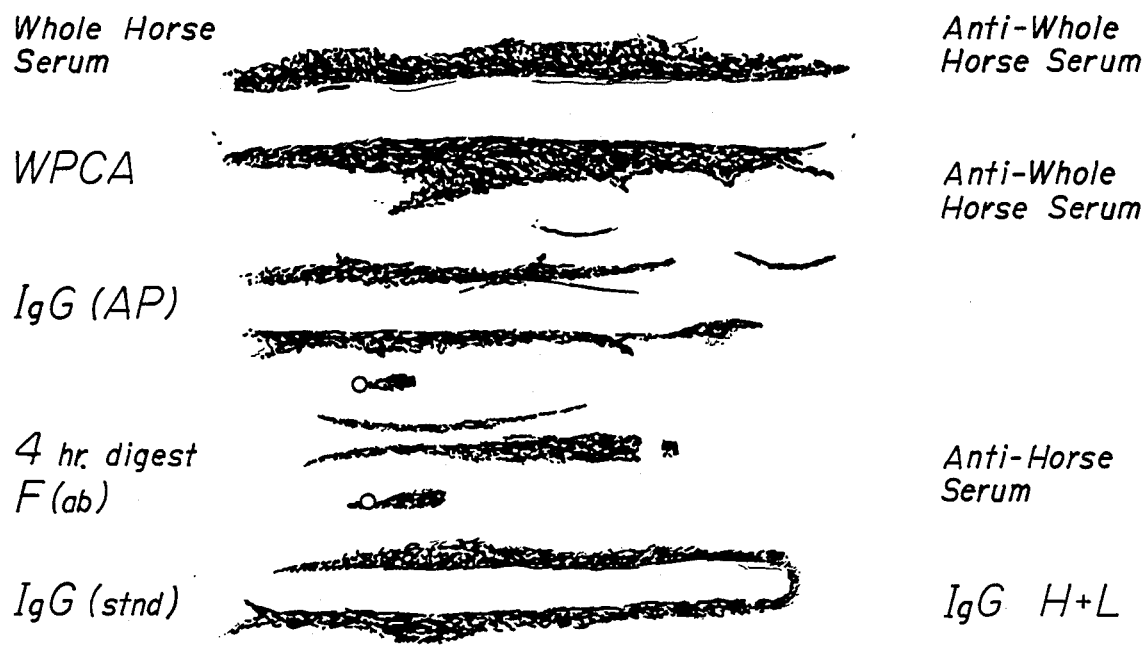
FIG. 3 depicts immunoelectrophoresis of whole equine serum.

The immunoelectrophoresis diagrams of FIG. 3 show that when Wyeth antivenin (WPCA) is reacted against anti-whole horse serum there are multiple precipitate bands. This indicates that the Wyeth antivenin contains many different proteins which are removed by the processes taught in this patent disclosure. The IgG (AP) against anti-whole horse serum shows one clear band. The 4 hour digest shows the same clear band. These diffusions do not show any reactions against the IgG heavy and light bands because the antibody material is derived from IgG(T). On the other hand, the IgG does show a reaction. This also indicates that Applicants' antibodies are much purer than the Wyeth antivenin.

Again taking the immunoelectrophoresis diagrams in conjunction, FIG. 4 indicates the results of another set of tests on the 4 hour digest antibody products of this invention. Again, another clear precipitate band against F(ab)2 is shown. A weak F(ab) reaction is noted along with a slight hint of a F(c) reaction. This would seem to indicate that a 100% digestion to F(ab) fragments was not accomplished in the 4 hour digestion period and that anti-F(c) reacts against the IgG(T) antibody. It is known from the literature on horse immunoglobulins that IgG and IgG(T) share common determinants on their F(c) portion. Consequently our preferred digestion period is in the 4 to 6 hour range.

Moreover, applicants have found that papain bound to polyacrylamide gel (e.g., using 108 mg in 5 ml of acrylamide-bisacrylamide monomer and Type III papain) will digest horse polyvalent antisera to F(ab) and F(c) fragments (this took 18 hours at 37° C. at the above concentration) just as it digests horse monovalent antisera. Likewise, the papain digests polyvalent IgG(T) to F(ab) and F(c) fragments. Furthermore, the papain need not be bound to polyacrylamide.

Figure 7:
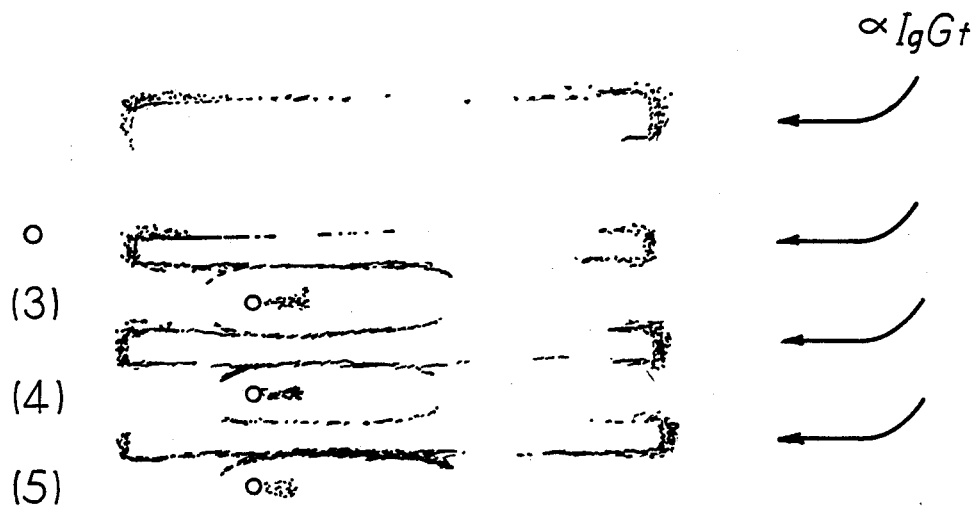
FIG. 7 depicts immunoelectrophoresis of 18 hour digest of F(ab) antibody materials from a polyvalent source.
Figure 7:
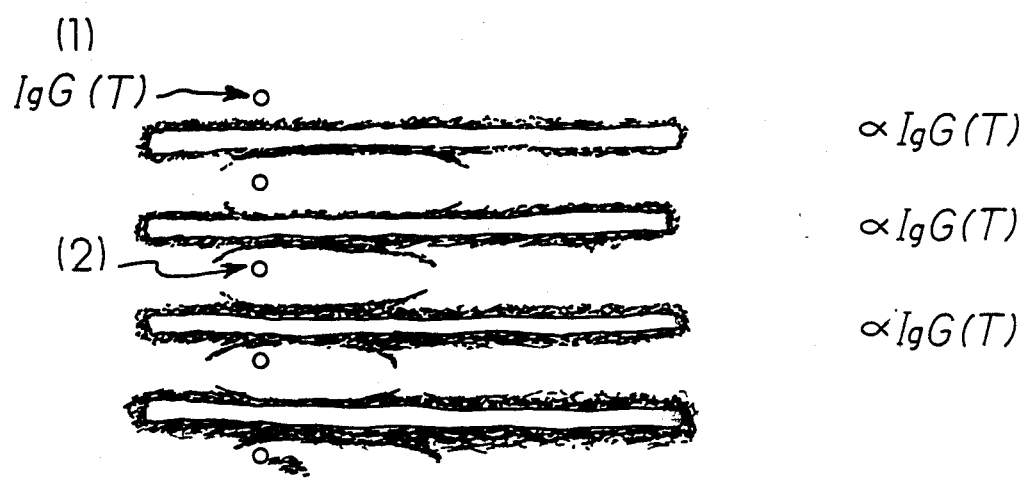

The proof of this particular digestion was established by immunoelectro-phoresing (IEP) anti-IgG(T) antibody against (1) polyvalent IgG(T) standard, traditional digest (see generally, Nisonoff, A. Methods Medical Res. 101:134-141, 1964), (2) polyvalent IgG(T) non-digested, (3) polyvalent anti-horse serum, traditional digest and (4) polyvalent anti-horse serum papain-polyacrylamide digest. Referring to the IEP Key shown in FIG. 7 we note that the standard IgG(T) IEP anti-IgG(T) shows one precipitin arc (i.e., #2 on the IEP Key). Polyvalent IgG(T) digested by a traditional method was immunoelectrophoresed against anti-IgG(T) shows two precipitin arcs corresponding to F(ab) and F(c) (i.e., #1 on the IEP Key of FIG. 7). Polyvalent anti-horse serum digested 18 hours with papain/polyacrylamide at 37° C. IEP against anti-IgG(T) shows two precipitin arcs corresponding to F(ab) and F(c) with some remaining IgG(T) (i.e., #5 on the IEP Key). Polyvalent anti-horse serum digested for 48 hours with papain bound to polyacrylamide at 37° C. IEP against anti-IgG(T) shows partial digestion to F(ab) and F(c) with remaining IgG(T) (i.e., #3 on the IEP Key). A schematic relationship showing each of the steps of the process of this invention, as applied to a polyvalent or monovalent antisera, is depicted in FIG. 8.

LETHALITY DETERMINATIONS

After establishing the intravenous $LD_{50}$ for each venom, the following lethality determinations were used to establish the efficacy of various antivenins prepared by the processes of this invention. Individual solutions of the venom-acrylamide purified antibodies, as well as those of the Wyeth ACP used in the comparisons, were allowed to stand for 30 minutes before use in these lethality determinations. Swiss-Webster mice, weighing 20-26 g, were administered the individual solutions by tail vein in volumes less than 100 ul. Results were interpreted at the end of 24 hours unless otherwise indicated. The F(ab) fragments and IgG issued in these lethality determinations were prepared by the processes previously discussed in this patent disclosure.

The first determination is a venom plus 1 Lethal Dose 99 ($LD_{99}$) of Crotalus atrox venom. Using the $LD_{99}$ dosage, 3 of 9 mice treated with Wyeth ACP antivenin were alive at the end of the 24 hour period. When an IgG produced from a bulk, unprocessed hyperimmune equine serum by the IgG purification process of this invention was employed as the antivenin, 6 of 9 mice survived the 24 hour period.

TABLE 1

Crotalus atrox
I.P.
Venom + $LD_{99}$ sample
($LD_{50}$ = 2.32 mg/kg)

| | (24 hrs.) | |
|---|---|---|
| | Alive | Dead |
| Venom | 0 | 5 |
| Venom + Wyeth | 3 | 6 |
| Venom + (IgG) | 6 | 3 |

Table 2 shows the results of using 2 times the $LD_{50}$ dose (2.32 mg/kg) and 4 times an equal weight of an F(ab) fragments antibody prepared from bulk unprocessed hyperimmune equine serum. As noted, these F(ab) fragments are the result of a 4 hour papain digestion.

TABLE 2

Crotalus viridis helleri
I.P.
2 × $LD_{50}$ × 4 × sample
($LD_{50}$ = 2.32 mg/kg)

| | (24 hrs) | |
|---|---|---|
| | Alive | Dead |
| Venom | 0 | 4 |
| Venom + Wyeth | 1 | 3 |
| 4 hr F (ab) | 3 | 1 |

Table 3 compares 48 hour digestion F(ab) fragments, IgG and 4 hour digestion F(ab) fragment antibodies to Wyeth ACP antivenin on the dosage basis indicated.

TABLE 3

Crotalus viridis helleri
I.P.
2 × $LD_{50}$ + twice that of the sample
($LD_{50}$ = 2.32 mg/kg)

| | 24 (hrs) | |
|---|---|---|
| | Alive | Dead |
| Venom | 0 | 4 |
| Venom + Wyeth | 1 | 3 |
| Venom + 48 hr F (ab) | 4 | 0 |
| Venom + IgG | 4 | 0 |
| Venom + 4 hr F (ab) | 4 | 0 |

Table 4 show the time elapsed until death when twice the $LD_{99}$ dose is administered is conjunction with twice the $LD_{50}$ test antibody material. Applicants are of the opinion that the reason that the F(ab) fragment antibodies (4 hour and 48 hour) significantly delayed the time of death beyond the time afforded by the IgG is found in the previously discussed concept of volume of distribution.

Since there is a dynamic relationship between the antibody and venom, some of the venom in the attaching and releasing dynamic relationship will diffuse out of the bloodstream because the venom has a volume of distribution similar to that of the F(ab) fragments. The IgG on the other hand is limited to the bloodstream. Consequently, the F(ab) can follow the venom as it diffuses and neutralize it in places beyond the blood stream.

TABLE 4

Crotalus viridis helleri
I.V.
Time-Study
$LD_{99}$ × 2 × $LD_{50}$ test material
($LD_{50}$ = 1.61 mg/kg)

| Venom | 15 min |
|---|---|
| | 18 min |
| | 19 min |
| | 17 min |
| Venom + Wyeth | 22 min |
| | 18 min |
| | 71 min |
| | 50 min |
| Venom + IgG | 90 min |
| | 36 min |
| | 48 min |
| | 50 min |
| Venom + 4 hr F (ab) | 106 min |
| | 72 min |
| | 122 min |
| | 6 hr |
| Venom + 48 hr F (ab) | 120 min |
| | 6 hr |
| | 120 min |
| | 8 hr 55 min |

The results of table 5 indicate that in this experiment, the 4 hour digest F(ab) fragments gave the best protection and the ACP antivenin afforded no protection. In this case the efficacy of the IgG was equal to that of the 48 hour digest F(ab) fragments.

TABLE 5

Crotalus viridis helleri
I.V.
2 × $LD_{50}$ + 4 × sample
($LD_{50}$ = 1.61 mg/kg)

| | (24 hrs) | | |
|---|---|---|---|
| | #Mice | #Alive | #Dead |
| Control | 4 | 0 | 4 |
| Antivenin (Wyeth) | 5 | 0 | 5 |
| Peak II, 48 hrs F (ab) | 5 | 3 | 2 |
| Peak II, 4 hrs F (ab) | 5 | 5 | 0 |
| IgG | 5 | 3 | 2 |

Table 6 summarizes the time until death results of using a $LD_{75}$ dosage against 2 times the $LD_{50}$ antibody test material.

TABLE 6

Crotalus viridis helleri
I.P.
$LD_{75}$ + 2 × $LD_{50}$ test material
($LD_{50}$ = 2.32 mg/kg)

| Venom | 84 min |
|---|---|
| | 62 min |
| | 4 hr |
| Venom + Wyeth | 6 hr |
| | 6 hr + |
| | 8 hr |
| | 8 hr |

TABLE 6-continued

*Crotalus viridis helleri*
I.P.
$LD_{75} + 2 \times LD_{50}$ test material
($LD_{50}$ = 2.32 mg/kg)

| | |
|---|---|
| Venom + IgG | 9 hr |
| | 24 hr alive |
| | 24 hr alive |
| | 8 hr |
| Venom + 4 hr F (ab) | 24 hr alive |
| | 24 hr alive |
| | 24 hr alive |
| Venom + 48 hr F (ab) | 8 hr |
| | 4 hr |
| | 24 hr alive |
| | 2 hr |

The above data indicates that the F(ab) fragments as well as IgG prepared by the processes of this invention can be used in the treatment of human snake bite victims. The dosages will be adjusted to suit the particular circumstances of the envenomation. In any event, the antibodies produced by this invention have specific activities much greater than that of Wyeth antivenin. The purified F(ab) is believed to be a protein having a molecular weight of about 50,000 Daltons. Furthermore, the F(ab) fragments produced from bulk, unprocessed hyperimmune equine serum appear to be the same as the F(ab) fragments which can be produced from Wyeth ACP purified by ammonium sulfate precipitation procedures. The purified IgG is believed to be a protein having a molecular weight of about 150,000. These antibodies clearly retain their activities after the purification steps of this invention. Furthermore, the therapeutically active portion of these materials remains while other portions of the original protein molecule which are antigenic to humans are removed by the processes of this invention. Hence anaphylaxis in individuals sensitive to horse serum and serum sickness reactions in general should be significantly reduced by use of these antivenins.

Thus having described our invention, we claim:

1. A process for isolating F(ab) fragments from an antibody containing source comprising: contacting the antibody containing source with a papain-polyacrylamide matrix to obtain a solution containing F(ab) and F(c) fragments; and passing the solution containing the F(ab) and F(c) fragments through an affinity chromatography system having a gel comprised of an antigen having an affinity for the F(ab) fragments and which is embedded in a polyacrylamide matrix, whereby the F(ab) fragments are isolated from the F(c) fragments for subsequent recovery.

2. The process of claim 1 wherein the antibody containing source is a bulk, unprocessed hyperimmune serum.

3. The process of claim 1 wherein the antibody containing source is a monoclonal antibody source.

4. The process of claim 1 wherein the antibody containing source is partially purified by precipitation procedures.

5. A process for isolating F(ab) fragments from an antibody containing source comprising: contacting the antibody containing source with a papain-polyacrylamide matrix to obtain a solution containing F(ab) and F(c) fragments; and passing the solution containing the F(ab) and F(c) fragments through an affinity chromatography system having a gel comprised of an antigen having an affinity for the F(c) fragments and which is embedded in a polyacrylamide matrix, whereby the F(ab) fragments are isolated from the F(c) fragments for subsequent recovery.

6. The process of claim 5 wherein the antibody containing source is a bulk, unprocessed hyperimmune serum.

7. The process of claim 5 wherein the antibody containing source is a monoclonal antibody source.

8. The process of claim 5 wherein the antibody containing source is partially purified by precipitation procedures.

9. A process for isolating $F(ab)_2$ fragments from an antibody containing source comprising: contacting the antibody containing source with a pepsin-polyacrylamide matrix to obtain a solution containing $F(ab)_2$ and F(c) fragments; and passing the solution containing the $F(ab)_2$ and F(c) fragments through an affinity chromatography system having a gel comprised of an antigen having an affinity for the $F(ab)_2$ fragments embedded in a polyacrylamide matrix, whereby the $F(ab)_2$ fragments are isolated from the F(c) fragments for subsequent recovery.

10. The process of claim 9 wherein the antibody containing source is a bulk, unprocessed hyperimmune serum.

11. The process of claim 9 wherein the antibody containing source is a monoclonal antibody source.

12. The process of claim 9 wherein the antibody containing source is partially purified by precipitation procedures.

13. A process for isolating $F(ab)_2$ fragments from a bulk antibody containing source comprising: contacting the antibody containing source with a pepsin-polyacrylamide matrix to obtain a solution containing $F(ab)_2$ and F(c) fragments; and passing the solution containing the $F(ab)_2$ and F(c) fragments through an affinity chromatography system having a gel comprised of an antigen having an affinity for the F(c) fragments embedded in a polyacrylamide matrix, whereby the $F(ab)_2$ fragments are isolated from the f(c) fragments for subsequent recovery.

14. The process of claim 13 wherein the antibody containing source is a bulk, unprocessed hyperimmune serum.

15. The process of claim 13 wherein the antibody containing source is a monoclonal antibody source.

16. The process of claim 13 wherein the antibody containing source is partially purified by precipitation procedures.

* * * * *